(12) United States Patent
Lombaert et al.

(10) Patent No.: US 8,007,437 B2
(45) Date of Patent: Aug. 30, 2011

(54) METHOD AND APPARATUS FOR INTERACTIVE 4-DIMENSIONAL (4D) VIRTUAL ENDOSCOPY

(75) Inventors: Herve Jun Alfred Lombaert, Montreal (CA); Frank Sauer, Princeton, NJ (US); Yiyong Sun, Lawrenceville, NJ (US); Chenyang Xu, Allentown, NJ (US)

(73) Assignee: Siemens Aktiengesellschaft, München ( * ) Notice: Subject to any disclaimer, the term of this patent is extended or adjusted under 35 U.S.C. 154(b) by 538 days.

(21) Appl. No.: 11/874,975

(22) Filed: Oct. 19, 2007

(65) Prior Publication Data

US 2008/0270095 A1    Oct. 30, 2008

Related U.S. Application Data (60) Provisional application No. 60/857,637, filed on Nov. 8, 2006.

(51) Int. Cl.
*A61B 8/00* (2006.01)
(52) U.S. Cl. ...................................................... 600/437
(58) Field of Classification Search .................. 600/437, 600/428, 413
See application file for complete search history.

(56) References Cited

U.S. PATENT DOCUMENTS

| 6,443,894 B1 * | 9/2002 | Sumanaweera et al. ....... 600/443 |
| 6,892,090 B2 * | 5/2005 | Verard et al. .................. 600/424 |
| 2005/0283075 A1 * | 12/2005 | Ma et al. ....................... 600/441 |

OTHER PUBLICATIONS

Kostas Anagnostou, Tim J. Atherton, Andrew E. Waterfall, "4D volume Rendering With The Shear Warp Factorisation", Proceedings of the 2000 IEEE Symposium on Volume Visualization. pp. 129-137, 2000.
Anna Vilanova i Bartroli, "Visualization Techniques for Virtual Endoscopy", PhD thesis, Technische Universität Wien, Sep. 2001; anna@cg.tuwien.ac.at; http://www.cgv.tugraz.at/; Abstract only enclosed (German and English).

* cited by examiner

*Primary Examiner* — Jacqueline Cheng
(74) *Attorney, Agent, or Firm* — Donald B. Paschburg (57) ABSTRACT

A method of performing 4-dimensional virtual endoscopy includes acquiring a sequence of cardiac images of a patient's heart from an imaging device; acquiring an electrocardiographic signal exhibiting cardiac cycles of the heart; and utilizing the electrocardiographic signal to gate the images for deriving respective 3-dimensional views in succession at corresponding cardiac cycles, from respective cardiac images at a selected phase point common to each of the corresponding cardiac cycles.

22 Claims, 6 Drawing Sheets

METHOD AND APPARATUS FOR INTERACTIVE 4-DIMENSIONAL (4D) VIRTUAL ENDOSCOPY

CROSS-REFERENCE TO RELATED APPLICATION AND CLAIM OF PRIORITY

Specific reference is hereby made to copending U.S. Provisional Patent Application No. 60/857,637, filed Nov. 8, 2006, in the names of inventors HERVE LOMBAERT, FRANK SAUER, YIYONG SUN, CHENYANG XU, and entitled Interactive 4D Virtual Endoscopy for Cardiac Imaging, and whereof the disclosure is hereby incorporated herein by reference and whereof the benefit of priority is claimed.

FIELD OF THE INVENTION

The invention relates generally to Interactive 4-dimensional (4D) imaging and, more particularly, to 4D Virtual Endoscopy for Cardiac Imaging.

BACKGROUND OF THE INVENTION

Virtual endoscopy allows visualization of a scene setup from pre-acquired data. Images are created with a virtual camera interactively manipulated by a user. Imaging techniques currently in use and how the acquired data is visualized are first briefly reviewed below.

At the present time, computed tomography (CT) and magnetic resonance (MR) imaging are the two popular imaging techniques used to capture images of a patient's anatomy, in accordance with known techniques. With CT, different X-ray images taken from a rotational scanner are used to reconstruct a 3D volume. Images of various portions and parts of the internal anatomy will generally appear in an image with different intensities. With MR resonance, relaxation times from excited hydrogen molecules are measured. Using the right parameters, it is possible to image different tissues. Both techniques provide serviceable resolution. In another promising 3D imaging technique, ultrasound is used to create images by localizing sound echoes from an ultrasound emitter. Recent hardware apparatus allows 3D acquisition of data.

It is also possible to interpolate 3D volumes with the composition of 2D ultrasound frames. Acquired data can be visualized in a volume renderer, in a virtual endoscopy, or as single slices. It can be any arbitrary slice, called multi-planar reconstruction (MPR). By manipulating these slices, it is possible to get a 3D sense of the volume. In a volume renderer, the data is directly displayed in 3D. It is possible to rotate around the volume, and to zoom or pan the volume. By rendering certain intensities of the data, different tissues can be revealed. As an additional help to seeing inside, the volume can be cut or intercepted by an arbitrary plane.

In a virtual endoscopy, a virtual camera is located inside the volume. The camera can be moved or rotated and it is possible to change the camera parameters such as its field of view. To define what constitutes a cavity in the volume, an iso-surface value is chosen. Intensities below this value will be considered a cavity, and intensities above it will be rendered as opaque. In the endoscopic view, the boundary seen will therefore be dependent on the iso-surface value.

To render a virtual endoscopic view, two methods can be used: ray casting and iso-surface visualization. The first method casts rays from the virtual camera and detects when the rays hit the volume. At the boundary, the surface normal is used to compute the correct lighting of the current pixel. Each ray will generate a pixel on the screen. The second method extracts an iso-surface from the volume, for instance. with the marching cube algorithm. The resulting mesh is placed in a 3D world and the virtual camera can navigate the mesh. This can be efficiently done with OpenGL, or any other suitable graphic language. Background information can be found in the literature: see, for example, the literature cited below.

The current state of the art visualization remains mostly static. For an extensive review of current endoscopic methods see, for example, Anna Vilanova i Bartroli, "Visualization Techniques for Virtual Endoscopy", PhD thesis, Technische Universitat Wien, September 2001.

A 4D volume renderer and dynamic MPR are currently available: see, for example, Kostas Anagnostou, Tim J. Atherton, Andrew E. Waterfall, "4D volume Rendering With The Shear Warp Factorisation", Proceedings of the 2000 IEEE Symposium on Volume Visualization. pp. 129-137, 2000; however, this material does not show a 4D virtual endoscopy system.

Textbooks useful in providing background material helpful to gaining a better understanding of the present invention include, for example, VIRTUAL ENDOSCOPY and RELATED 3D TECHNIQUES by P. Rogalla et al., Springer, Berlin & New York, 2002, FUNDAMENTALS OF IMAGE PROCESSING by Arthur R. Weeks, SPIE Optical Engineering Press & IEEE Press; 1996; IMAGE PROCESSING, ANALYSIS, AND MACHINE VISION, Second Edition, by Milan Sonka et al., PWS Publishing; 1999; and DIGITAL IMAGE PROCESSING, Second Edition, by Rafael C. Gonzalez et al., Prentice Hall; 2002.

SUMMARY OF THE INVENTION

In accordance with an aspect of the present invention, wherein a 4D visualization corresponds to three dimensions plus time, endoscopic visualization utilizes cardiac imaging data, such as from Computed Tomography (CT), Magnetic Resonance (MR), or Ultrasound (US) imaging. The system allows the visualization of a dynamic scene from inside the heart and can be used as a diagnostic tool or for surgery planning. Compared to 3D static endoscopic visualization, the system provides more visual information to the user.

In accordance with an aspect of the present invention a system for 4D (3D+time) endoscopic visualization uses cardiac imaging data, such as Computed Tomography, Magnetic Resonance, or Ultrasound Imaging. A system in accordance with the present invention allows the visualization of a dynamic scene as observed from inside the heart. It can be used in diagnostics or for surgery planning. As compared to 3D static endoscopic visualization, the system provides more visual information to the user.

In accordance with an aspect of the invention, a method of 4-dimensional virtual endoscopy includes acquiring a sequence of cardiac images of a patient's heart from an imaging device; acquiring an electrocardiographic signal exhibiting cardiac cycles of the heart; and utilizing the electrocardiographic signal to gate the images for deriving respective 3-dimensional views in succession at corresponding cardiac cycles, from respective cardiac images at a selected phase point common to each of the corresponding cardiac cycles.

In accordance with another aspect of the invention, the step for deriving respective 3D views includes placing the cardiac images in a 3D space and reconstructing a volume.

In accordance with another aspect of the invention, the step of acquiring an electrocardiographic signal includes a step of detecting the cardiac cycles and a step of interactively selecting the phase point.

In accordance with another aspect of the invention, the step for deriving respective 3D views utilizes one of (a) a ray casting algorithm and (b) a mesh extraction algorithm.

In accordance with another aspect of the invention the step for deriving a series of respective 3D views includes amending a 3D view so as to produce the next 3D view in the succession.

In accordance with another aspect of the invention, the step for deriving a series of respective 3D views includes a step of sensing breathing of the patient and excluding images not in the same phase of the respiratory cycle.

In accordance with another aspect of the invention, the step for deriving a series of respective 3D views includes a step of sensing sudden catheter movements in the patient and excluding images where such a sudden motion occurs.

In accordance with another aspect of the invention, the step for acquiring a sequence of cardiac images includes: a step of utilizing a virtual camera; and a step of virtually attaching the virtual camera to a wall image of the patient's heart so as to produce a substantially steady image of the heart.

In accordance with another aspect of the invention, a method of 4-dimensional (4D) virtual endoscopy, comprises: acquiring a motion signal of a patient's organ exhibiting motion cycles of the organ; acquiring a sequence of 3-dimensional (3D) images of the organ from an imaging device; utilizing the motion signal to gate the images for deriving respective 3D views in succession at corresponding motion cycles, from respective organ images at a selected phase point common to each of the corresponding motion cycles.

In accordance with another aspect of the invention, the step for acquiring a sequence of 3D views includes one of: (a) utilizing a real-time 3D ultrasound imaging device with multiple transducer arrays, and (b) utilizing a tracked ultrasound imaging device collecting data over space.

In accordance with another aspect of the invention, the step of utilizing a tracked ultrasound imaging device collecting data over space comprises utilizing an Acunav™ system.

In accordance with another aspect of the invention, a system for performing 4-dimensional (4D) virtual endoscopy, comprises: a memory device for storing a program and other data; and a processor in communication with the memory device, the processor operative with the program to perform: acquiring a sequence of cardiac images of a patient's heart from an imaging device; acquiring an electrocardiographic signal exhibiting cardiac cycles of the heart; and utilizing the electrocardiographic signal to gate the images for deriving respective 3-dimensional (3D) views in succession at corresponding cardiac cycles, from respective cardiac images at a selected phase point common to each of the corresponding cardiac cycles.

In accordance with another aspect of the invention, a system for performing 4-dimensional (4D) virtual endoscopy, comprises: apparatus for acquiring a motion signal of a patient's organ exhibiting motion cycles of the organ; apparatus for acquiring a sequence of 3-dimensional (3D) images of the organ from an imaging device; and apparatus for utilizing the motion signal to gate the images for deriving respective 3D views in succession at corresponding motion cycles, from respective organ images at a selected phase point common to each of the corresponding motion cycles.

In accordance with another aspect of the invention, a computer program product comprises a computer useable medium having computer program logic recorded thereon for program code for performing 4-dimensional (4D) virtual endoscopy, comprising: acquiring a sequence of cardiac images of a patient's heart from an imaging device; acquiring an electrocardiographic signal exhibiting cardiac cycles of the heart; and utilizing the electrocardiographic signal to gate the images for deriving respective 3-dimensional (3D) views in succession at corresponding cardiac cycles, from respective cardiac images at a selected phase point common to each of the corresponding cardiac cycles.

BRIEF DESCRIPTION OF THE DRAWINGS

The invention will be more fully understood from the following detailed description, in conjunction with the drawings, in which.

DETAILED DESCRIPTION OF THE INVENTION

For greater clarity, the present invention will be described in terms of exemplary embodiments; however, it will be understood that the particulars of a specific exemplary embodiment are not intended to limit the invention but rather to aid in the description. It will be understood that references in the present context to, for example, a camera and camera attachment generally refer to virtual equivalents.

In accordance with an aspect of the present invention, a general framework for a method and system for an interactive 4D virtual endoscopy system includes:

reconstructing the 4D volume from a 3D image;

rendering a dynamic endoscopic scene;

interactively manipulating the virtual endoscope; and interactively tuning parameters of the system.

4D CT and MR volumes are obtained from the scanner in a straightforward way. Descriptions of such methods are available in the literature and need not be repeated herein in detail. Accordingly, in the description of embodiments of the invention herein, the manner of how to reconstruct a 4D volume using 3D ultrasound (US) images will be described. Ultrasound sequences are acquired with either a real-time 3D ultrasound with multiple transducer arrays, or with a tracked Acunav™ collecting data over space. Images thus acquired are placed in a 3D space to reconstruct the volume. In conjunction with the applicable electrocardiogram signal (ECG), US frames are gated and multiple 3D volumes are created from frames corresponding to the same cardiac phases. The result is a reconstructed 4D volume.

Rendering of a dynamic scene requires the use of a different 3D data set at each successive frame, as will also be illustrated below in reference to FIGS. 1 and 2. The system in accordance with the present invention uses a single 3D volume to generate the endoscopic view, and changes the 3D volume at each new time step. Each single image generation can use any virtual endoscopy imaging. It can be, for instance, a ray casting or a mesh extraction algorithm as described in the previous section. The algorithm can also be hardware accelerated for smooth visualization of the dynamic scene.

As with static virtual endoscopy, the endoscope can be manipulated interactively by the user. An embodiment in accordance with the invention includes the commands of camera rotation; camera translation; camera tilting; and camera field of view selection.

An embodiment of the system in accordance with the invention also includes renderer parameter tuning items such as:
  changing the iso-surface value;
  changing the iso-surface color;
  changing the lighting and the field of view;
  changing the image resolution; and
  smoothing the rendered data (e.g. by the use of an average or median filter).

These camera and renderer intrinsic properties can be saved and loaded. Presets are also made available. For instance, after a volume loading, the camera can be automatically placed in the left atrium and pointing toward the pulmonary veins. The system in accordance with the invention can handle different modalities such as, for instance CT, MR or 3D compounded ultrasound. Each modality requires parameter tuning items which are provided with the available presets.

Additionally, an embodiment of the system in accordance with the invention provides temporal commands, which may include commands such as:
  a temporal navigation bar including a play and pause button, a stop button, a fast forward button, and a fast rewind button;
  a command to record the endoscopic view in a movie file; and
  a command to change the frame rate of the dynamic scene.

These controls are used to understand the dynamics involved in the scene. They can be used for diagnostics. For instance, motion abnormalities can be detected with frame by frame analysis.

Furthermore an embodiment of the system in accordance with the present invention comprises features such as real time virtual endoscopy; with ultrasound, acquisition can be done in real-time—the latest available 3$d$ volume can be used in the rendering algorithm.

As the scene is dynamic, it becomes hard to have a steady visualization of a fast moving structure. it is contemplated to "bind" the camera position with a surface point on the wall where the camera would move with this point so that it will appear static on the screen. Accordingly, an embodiment of the present invention may include a feature of attaching the camera to the wall or surface in the image which, for example in the case of the heart, can be the endocardium.

Temporal markers may also be provided wherein a point on the surface can be marked and later tracked over time, thus allowing the visualization and analysis of a landmark motion.

Collision detection may also be provided such that when the user moves the camera, the system detects the camera colliding with the iso-surface of a certain volume so that the camera cannot be moved across the iso-surface.

The use of an efficient 4D path generation algorithm provides for easier navigation in the heart as it will constrain the camera inside the heart at all times.

Figure 1:
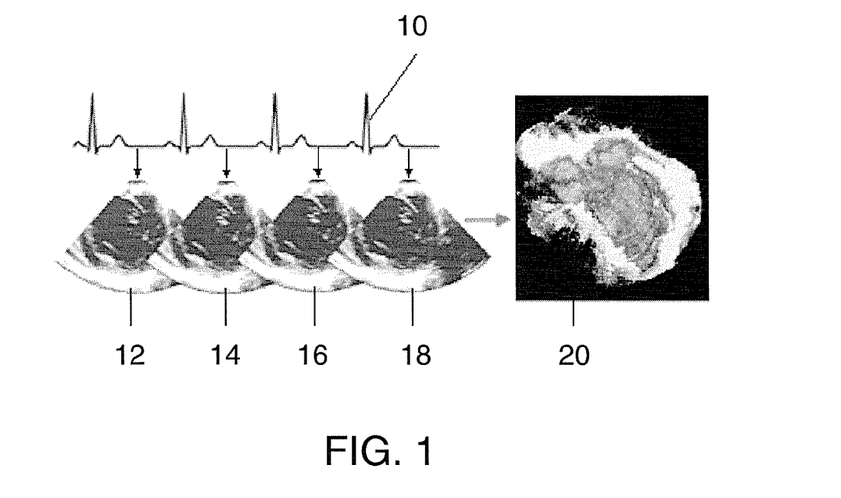
FIG. 1 shows the reconstruction of a plurality of 3D volumes at corresponding different cardiac cycles from frames of the same given cardiac phase in the respective cardiac cycles in accordance with principles of the present invention.
Figure 2:
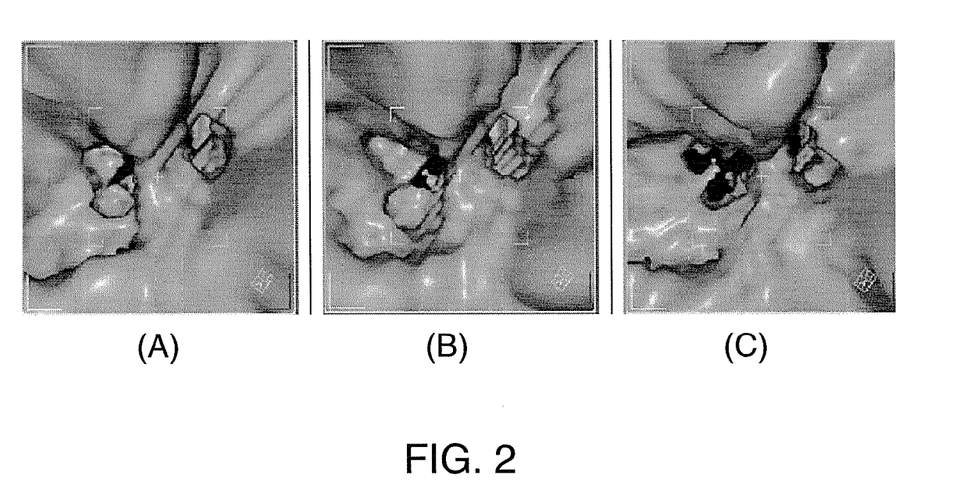
FIG. 2 shows successively generated views for virtual endoscopy in accordance with the present invention.

In the case of using a 3D ultrasound image, testing was performed using the intracardiac echo, as shown in FIGS. 1 and 2. FIG. 1 shows the reconstruction of a plurality of 3D volumes at corresponding different cardiac cycles from frames of the same given cardiac phase in the respective cardiac cycles. Reference numeral 10 indicates cardiac cycle waveforms used for gating, with sagittal lines pointing to the respective frames 12-18 below. A representative reconstructed 3D volume corresponding to a given frame is indicated by numeral 20.

FIG. 2 shows successively generated views (A), (B) and (C) for virtual endoscopy.

While the foregoing illustrative example utilizes the intracardiac echo, clearly the method of the present invention also applies to a general cardiac echocardiogram.

Further understanding of the operation of representative embodiments of the present invention is provided by FIGS. 3-7, which provide flow charts of aspects of the method of the present invention.

Figure 3:
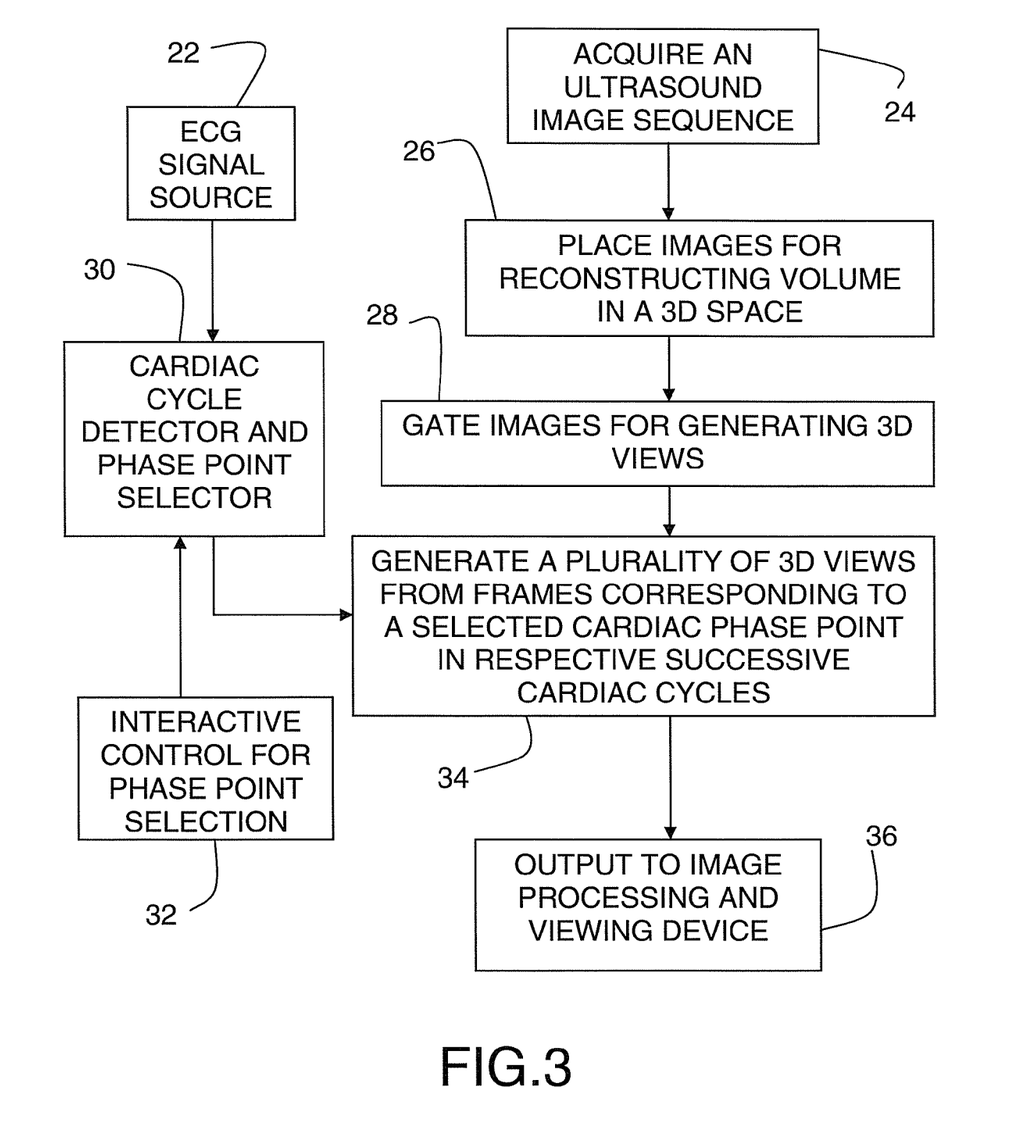
FIGS. 3-7 show schematic flow diagrams of steps in accordance with principles of the present invention.

FIG. 3 shows an ECG signal source 22 providing a waveform signal to a cardiac cycle detector and phase point selector 30 which is coupled to an interactive control 32 for phase point selection. An ultrasound image sequence is acquired in 24 and the images are placed in a 3D space in 26, where volume images are reconstructed and are then gated at 28. In cooperation with a signal from selector 30, a plurality of 3D views is generated at 34 from frames corresponding to a selected cardiac phase point in respective successive cardiac cycles, and thence outputted at 36.

Figure 4:
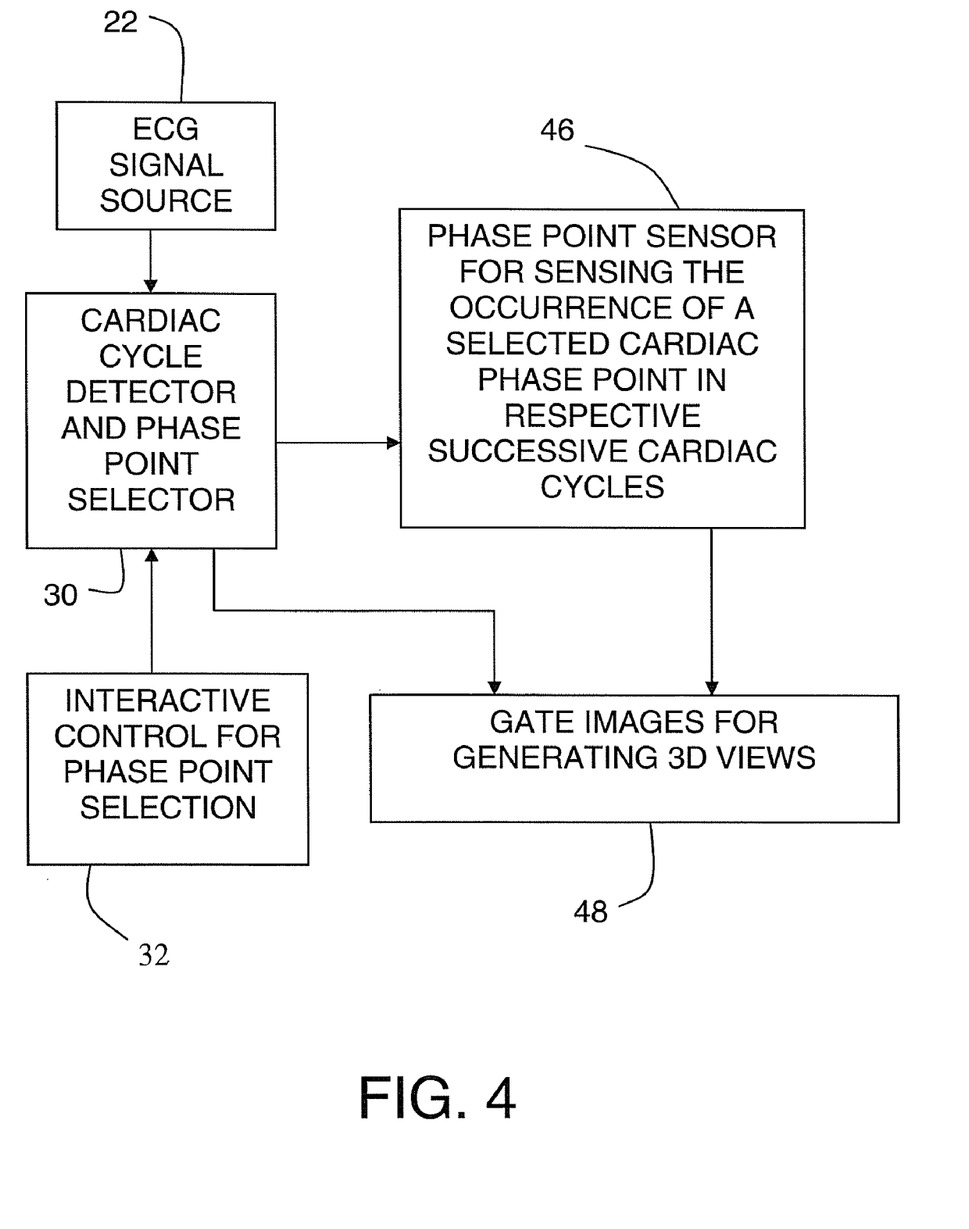

FIG. 4 shows an ECG signal source 22 providing a waveform signal to a cardiac cycle detector and phase point selector 30 which is coupled to an interactive control 32 for phase point selection. At 46, the occurrence is sensed of a selected cardiac phase point in respective successive cardiac cycles. A gating signal from selector 30 enables gating images at 48 for generating 3D views.

Figure 5:
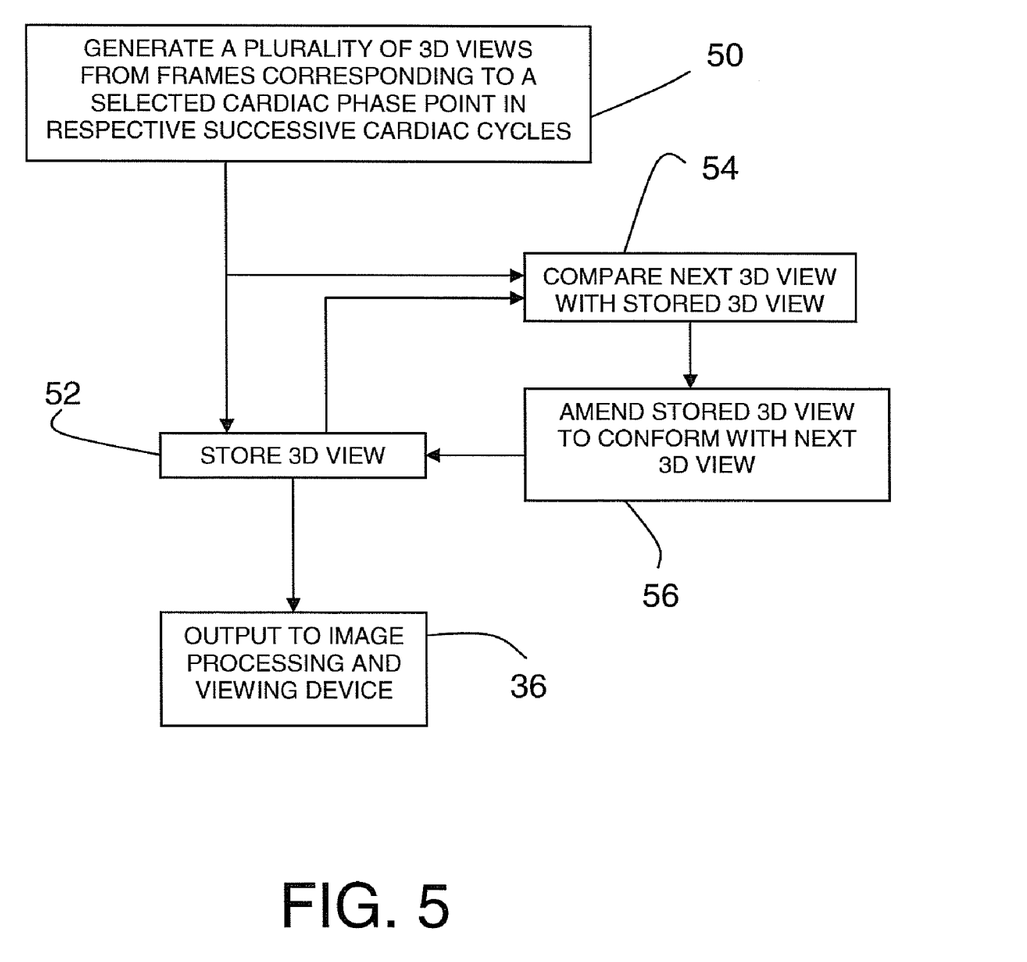

In FIG. 5, a plurality of 3D views is generated at 50 from frames corresponding to a selected cardiac phase point in respective successive cardiac cycles and 3D views are stored at 52. A comparison is made at 54 between the stored view and the next or succeeding view. The stored view is then amended at 56 to conform it to the next view.

Figure 6:
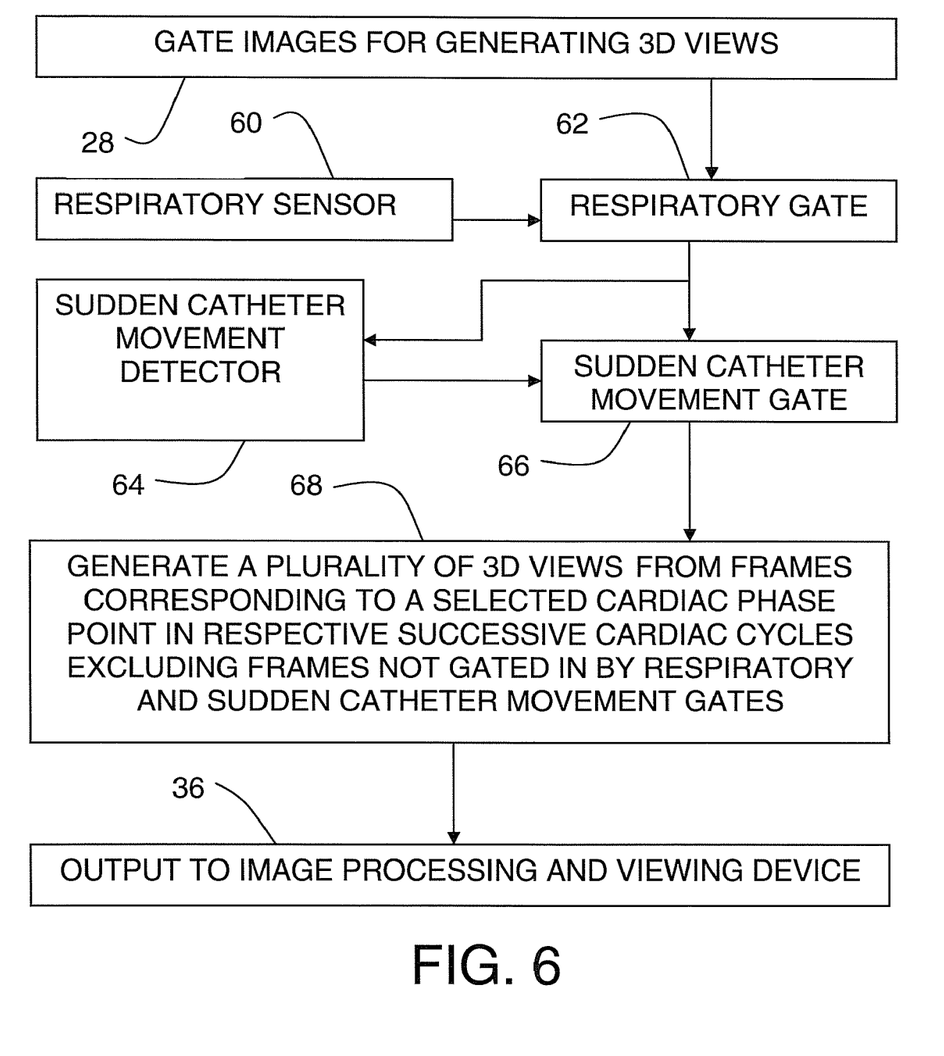

FIG. 6 shows the gating of images at 28 for generating 3D views. A signal from a respiratory sensor 60 is applied to a respiratory gate 62 for corresponding gating of images. A detector 64 for sudden catheter movements provides a signal representative of such sudden movements for a gating function at 66, so that at 68 a plurality of 3D views is generated from frames corresponding to a selected cardiac phase point in respective successive cardiac cycles excluding frames not gated in by respiratory and sudden catheter movement gates. The views are outputted at 36 to image processing and viewing devices.

Figure 7:
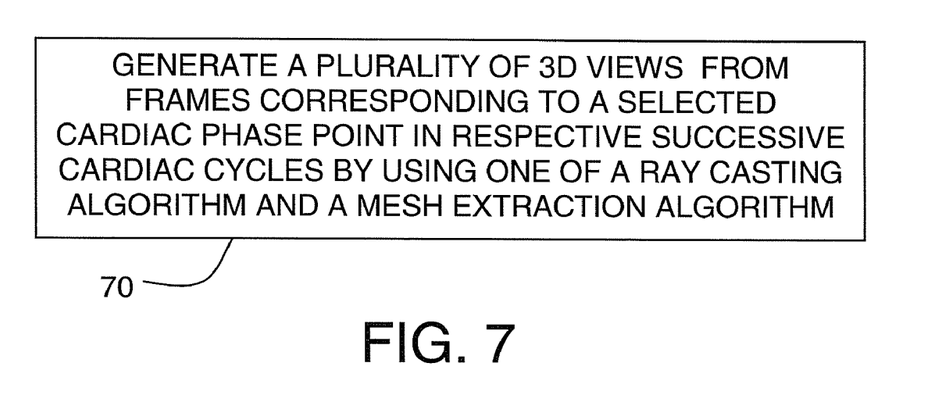

FIG. 7 shows the generation of a plurality of 3D views at 70 from frames corresponding to a selected cardiac phase point in respective successive cardiac cycles by using a ray casting algorithm or a mesh extraction algorithm.

Figure 8:
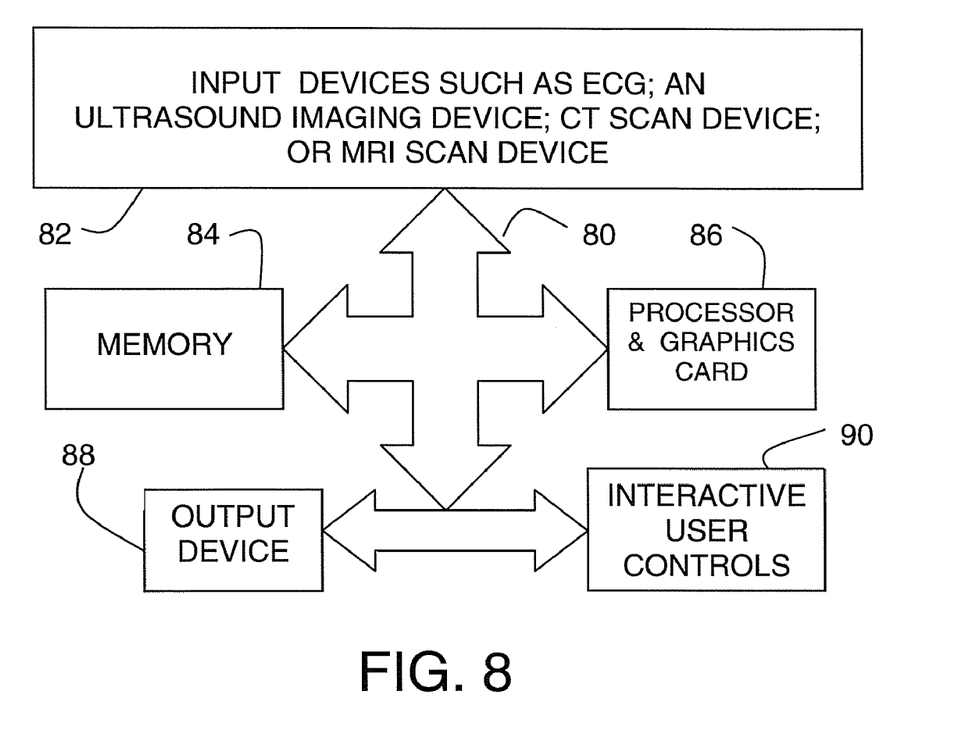
FIG. 8 shows in block schematic form the application of a digital computer in the present invention.

As will be apparent, the present invention is best intended to be implemented with the use and application of imaging equipment in conjunction with a programmed digital computer. FIG. 8 shows in basic schematic form a digital processor coupled for two way data communication with an input device, an output device, and a memory device, in applications for embodiments of the present invention. Data buss 80 couples input devices at 82, such as an ECG, an ultrasound device or a CT scan device or MRI scan device to a processor 86 and graphics card, a memory 84, an output device 88, and interactive user controls 90.

The memory device is generally used for storing a program and other data. The input device is so designated in broad terms as a device for providing an appropriate image or images for processing in accordance with the present invention. For example, the input may be from an imaging device, such as a device incorporated in a CATSCAN, X-ray machine, an MRI or other device, or a stored image, or by communication with another computer or device by way of direct connection, a modulated infrared beam, radio, land line, facsimile, or satellite as, for example, by way of the World Wide Web or Internet, or any other appropriate source of such data. The output device may include a computer type display device using any suitable apparatus such as a cathode-ray kinescope tube, a plasma display, liquid crystal display, and so forth, or it may or may not include a device for rendering an image and may include a memory device or part of the memory device of FIG. 8 for storing an image for further processing, or for viewing, or evaluation, as may be convenient, or it may utilize a connection or coupling including such as are noted above in relation to the input device. The processor is operative with a program set up in accordance with the present invention for implementing steps of the invention. Such a programmed computer may interface readily through communications media such as land line, radio, the Internet, and so forth for image data acquisition and transmission.

The invention may be readily implemented, at least in part, in a software memory device and packaged in that form as a software product. This can be in the form of a computer program product comprising a computer useable medium having computer program logic recorded thereon for program code for performing the method of the present invention.

The present invention is not limited to cardiac applications. For convenience, embodiments were described in a cardiac setting for illustrative purposes, but the invention is applicable to other body parts with periodic movements such as, for example, respiratory motion.

The present invention has also been explained in part by way of examples using illustrative exemplary embodiments. It will be understood that the description by way of exemplary embodiments is not intended to be limiting and that, while the present invention is broadly applicable, it is helpful to also illustrate its principles, without loss of generality, by way of exemplary embodiments.

It will also be understood that various changes and substitutions not necessarily herein explicitly described may be made by one of skill in the art to which it pertains. Such changes and substitutions may be made without departing from the spirit and scope of the invention which is defined by the claims following.

What is claimed is:

1. A method of performing 4-dimensional (4D) virtual endoscopy, comprising:
    acquiring a sequence of cardiac images of a patient's heart from an imaging device;
    acquiring an electrocardiographic signal exhibiting cardiac cycles of said heart;
    utilizing said electrocardiographic signal to gate said images for deriving respective 3-dimensional (3D) views in succession at corresponding cardiac cycles, from respective cardiac images at a selected phase point common to each of said corresponding cardiac cycles so as to provide a 3 dimensional visualization of said patient's heart as a function of time for said 4D virtual endoscopy;
    utilizing a virtual camera; and
    virtually attaching said virtual camera to a point selected on a wall or surface in said sequence of cardiac images of said patient's heart, such that said virtual camera moves together with said point and will appear static in said respective 3D views in succession so as to provide said 3-dimensional visualization of said patient's heart as a function of time for said 4D virtual endoscopy, so as to produce a substantially steady image of said heart.

2. A method in accordance with claim 1, wherein said step for deriving respective 3D views includes placing said cardiac images in a 3D space and reconstructing a volume.

3. A method in accordance with claim 1, wherein said step of acquiring an electrocardiographic signal includes a step of detecting said cardiac cycles and a step of interactively selecting said phase point.

4. A method in accordance with claim 1, wherein said step for deriving respective 3D views utilizes one of (a) a ray casting algorithm and (b) a mesh extraction algorithm.

5. A method in accordance with claim 1, wherein said step for deriving respective 3D views in succession includes amending a 3D view so as to produce the next 3D view in said succession.

6. A method in accordance with claim 1, wherein said step for deriving respective 3D views includes a step of sensing breathing of said patient and excluding ones of said images affected by said breathing.

7. A method in accordance with claim 1, wherein said step for deriving respective 3D views includes a step of sensing breathing and respiratory cycles of said patient and excluding images not in the same phase of a respiratory cycle.

8. A method in accordance with claim 1, wherein said step for deriving respective 3D views includes a step of sensing sudden catheter movements in said patient and excluding ones of said images affected by said sudden catheter movements.

9. A method of performing 4-dimensional (4D) virtual endoscopy, comprising:
    acquiring a motion signal of a patient's organ exhibiting motion cycles of said organ;
    acquiring a sequence of 3-dimensional (3D) images of said organ from an imaging device;
    utilizing said motion signal to gate said images for deriving respective 3D views in succession at corresponding motion cycles, from respective organ images at a selected phase point common to each of said corresponding motion cycles so as to provide a 3 dimensional visualization of said patient's organ as a function of time for said 4D virtual endoscopy;
    utilizing a virtual camera; and
    virtually attaching said virtual camera to a point selected on a wall or surface in said sequence of organ images of said patient's organ, such that said virtual camera moves together with said point and will appear static in said respective 3D views in succession so as to provide said 3-dimensional visualization of said patient's organ as a function of time for said 4D virtual endoscopy, so as to produce a substantially steady image of said organ.

10. A method in accordance with claim 9, wherein said step of acquiring a sequence of 3D images includes one of:
    (a) utilizing a real-time 3D ultrasound imaging device with multiple transducer arrays, and
    (b) utilizing a tracked ultrasound imaging device collecting data over space.

11. A method in accordance with claim 9, wherein said step of acquiring a motion signal includes a step of detecting said motion cycles and a step of interactively selecting said phase point.

12. A method in accordance with claim 9, wherein said step of deriving respective 3D views includes amending a 3D view so as to produce the next 3D view in said succession.

13. A method in accordance with claim 9, wherein said step of deriving respective 3D views includes a step of sensing breathing of said patient and excluding ones of said images affected by said breathing.

14. A method in accordance with claim 9, wherein said step of deriving respective 3D views includes a step of sensing sudden catheter movements in said patient and excluding ones of said images affected by said sudden catheter movements.

15. A system for performing 4-dimensional (4D) virtual endoscopy, comprising:
   a non-transitory memory device for storing a program and other data; and
   a processor in communication with said memory device, said processor operative with said program to perform:
      acquiring a sequence of cardiac images of a patient's heart from an imaging device;
      acquiring an electrocardiographic signal exhibiting cardiac cycles of said heart;
      utilizing said electrocardiographic signal to gate said images for deriving respective 3-dimensional (3D) views in succession at corresponding cardiac cycles, from respective cardiac images at a selected phase point common to each of said corresponding cardiac cycles so as to provide a 3 dimensional visualization of said patient's heart as a function of time for said 4D virtual endoscopy;
      utilizing a virtual camera; and
      virtually attaching said virtual camera to a point selected on a wall or surface in said sequence of cardiac images of said patient's heart, such that said virtual camera moves together with said point and will appear static in said respective 3D views in succession so as to provide said 3-dimensional visualization of said patient's heart as a function of time for said 4D virtual endoscopy, so as to produce a substantially steady image of said heart.

16. A system in accordance with claim 15, wherein said step for deriving respective 3D views includes placing said cardiac images in a 3D space and reconstructing a volume.

17. A system in accordance with claim 15, wherein said step of acquiring an electrocardiographic signal includes a step of detecting said cardiac cycles and a step of interactively selecting said phase point.

18. A system in accordance with claim 15, wherein said step for deriving respective 3D views utilizes one of (a) a ray casting algorithm and (b) a mesh extraction algorithm.

19. A system in accordance with claim 15, wherein said step for deriving respective 3D views includes amending a 3D view so as to produce the next 3D view in said succession.

20. A system for performing 4-dimensional (4D) virtual endoscopy, comprising:
   means for acquiring a motion signal of a patient's organ exhibiting motion cycles of said organ;
   means for acquiring a sequence of 3-dimensional (3D) images of said organ from an imaging device; and
   a processor configured for:
      utilizing said motion signal to gate said images for deriving respective 3D views in succession at corresponding motion cycles, from respective organ images at a selected phase point common to each of said corresponding motion cycles so as to provide a 3 dimensional visualization of said patient's organ as a function of time for said 4D virtual endoscopy;
      utilizing a virtual camera; and
      virtually attaching said virtual camera to a point selected on a wall or surface in said sequence of organ images of said patient's organ, such that said virtual camera moves together with said point and will appear static in said respective 3D views in succession so as to provide said 3-dimensional visualization of said patient's organ as a function of time for said 4D virtual endoscopy, so as to produce a substantially steady image of said organ.

21. A computer program product comprising a computer useable non-transitory medium having executable computer program logic recorded thereon for program code for performing 4-dimensional (4D) virtual endoscopy, comprising:
   acquiring a sequence of cardiac images of a patient's heart from an imaging device;
   acquiring an electrocardiographic signal exhibiting cardiac cycles of said heart;
   utilizing said electrocardiographic signal to gate said images for deriving respective 3-dimensional (3D) views in succession at corresponding cardiac cycles, from respective cardiac images at a selected phase point common to each of said corresponding cardiac cycles so as to provide a 3 dimensional visualization of said patient's heart as a function of time for said 4D virtual endoscopy;
   utilizing a virtual camera; and
   virtually attaching said virtual camera to a point selected on a wall or surface in said sequence of cardiac images of said patient's heart, such that said virtual camera moves together with said point and will appear static in said respective 3D views in succession so as to provide said 3-dimensional visualization of said patient's heart as a function of time for said 4D virtual endoscopy, so as to produce a substantially steady image of said heart.

22. A computer program product in accordance with claim 21, wherein said step of acquiring an electrocardiographic signal includes a step of detecting said cardiac cycles and a step of interactively selecting said phase point; and wherein said step for deriving a series of respective 3D views includes amending a 3D view so as to produce the next 3D view in said succession.

* * * * *